United States Patent
Silvano de Sousa et al.

(10) Patent No.: US 9,903,816 B2
(45) Date of Patent: Feb. 27, 2018

(54) PHOTONIC CRYSTAL SENSOR STRUCTURE AND A METHOD FOR MANUFACTURING THE SAME

(71) Applicant: Infineon Technologies AG, Neubiberg (DE)

(72) Inventors: Jonathan Silvano de Sousa, Vienna (AT); Thomas Grille, Villach (AT); Ursula Hedenig, Villach (AT); Thomas Neidhart, Klagenfurt (AT); Peter Irsigler, Obernberg/Inn (AT); Vijaye Kumar Rajaraman, Villach (AT)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 14/557,584

(22) Filed: Dec. 2, 2014

(65) Prior Publication Data
US 2016/0153907 A1    Jun. 2, 2016

(51) Int. Cl.
| | |
|---|---|
| *G01N 21/59* | (2006.01) |
| *G01N 21/3504* | (2014.01) |
| *G01L 7/08* | (2006.01) |
| *G02B 6/12* | (2006.01) |
| *G02B 6/125* | (2006.01) |
| *G01K 11/00* | (2006.01) |

(52) U.S. Cl.
CPC ............ *G01N 21/59* (2013.01); *G01K 11/00* (2013.01); *G01L 7/086* (2013.01); *G01N 21/3504* (2013.01); *G02B 6/12004* (2013.01); *G02B 6/125* (2013.01); *G01N 2201/062* (2013.01); *G02B 2006/12166* (2013.01)

(58) Field of Classification Search
CPC ........... G01N 21/3504; G01N 21/1702; G01N 21/1704; G01N 21/61; G01N 2021/8578; G02F 202/32
See application file for complete search history.

(56) References Cited

U.S. PATENT DOCUMENTS

| | | | |
|---|---|---|---|
| 4,678,904 A | 7/1987 | Saaski et al. | |
| 7,305,161 B2 * | 12/2007 | Zhou | ..... G02B 6/1225 385/147 |
| 7,352,466 B2 * | 4/2008 | Cao | ......... B82Y 20/00 356/437 |

(Continued)

FOREIGN PATENT DOCUMENTS

| | | |
|---|---|---|
| CN | 1898592 A | 1/2007 |
| CN | 1942794 A | 4/2007 |

(Continued)

*Primary Examiner* — Kara E Geisel
*Assistant Examiner* — Violeta A Prieto
(74) *Attorney, Agent, or Firm* — Viering, Jentschura & Partner mbB

(57) ABSTRACT

A sensor and methods of making a sensor are disclosed. The sensor may include a substrate, an optical source, an optical detector, a plurality of optical cavities in the substrate or in a layer structure over the substrate, where the plurality of optical cavities may be arranged in an optical path between the optical source and the optical detector, and a processing circuit coupled to the optical detector and configured to receive a signal representing an optical signal received by the optical detector.

24 Claims, 17 Drawing Sheets

(56) References Cited

U.S. PATENT DOCUMENTS

| | | | | |
|---|---|---|---|---|
| 7,505,653 B2* | 3/2009 | Zhou | ............... | G02B 6/1225 385/125 |
| 7,973,924 B2* | 7/2011 | Noda | ............... | B82Y 20/00 356/300 |
| 2006/0193596 A1* | 8/2006 | Zhou | ............... | G02B 6/1225 385/147 |
| 2006/0285114 A1* | 12/2006 | Cao | ............... | B82Y 20/00 356/437 |
| 2007/0297740 A1* | 12/2007 | Zhou | ............... | B82Y 20/00 385/129 |
| 2008/0252890 A1* | 10/2008 | Noda | ............... | B82Y 20/00 356/436 |
| 2009/0153843 A1 | 6/2009 | Wang et al. | | |
| 2013/0284928 A1* | 10/2013 | Frey | ............... | B82Y 20/00 250/338.5 |
| 2015/0102372 A1* | 4/2015 | Dehe | ............... | H01L 33/44 257/98 |

FOREIGN PATENT DOCUMENTS

| | | |
|---|---|---|
| CN | 101458210 A | 6/2009 |
| CN | 103245635 A | 8/2013 |
| CN | 103616348 A | 3/2014 |
| CN | 104048942 A | 9/2014 |
| CN | 104075754 A | 10/2014 |
| EP | 2389014 A1 | 11/2011 |
| EP | 2338287 B1 | 7/2013 |
| JP | 0727696 A | 1/1995 |
| KR | 20090105757 A | 10/2009 |
| WO | 2005089129 A2 | 9/2005 |
| WO | 2006098844 A1 | 9/2006 |
| WO | 2007064702 A1 | 6/2007 |

\* cited by examiner

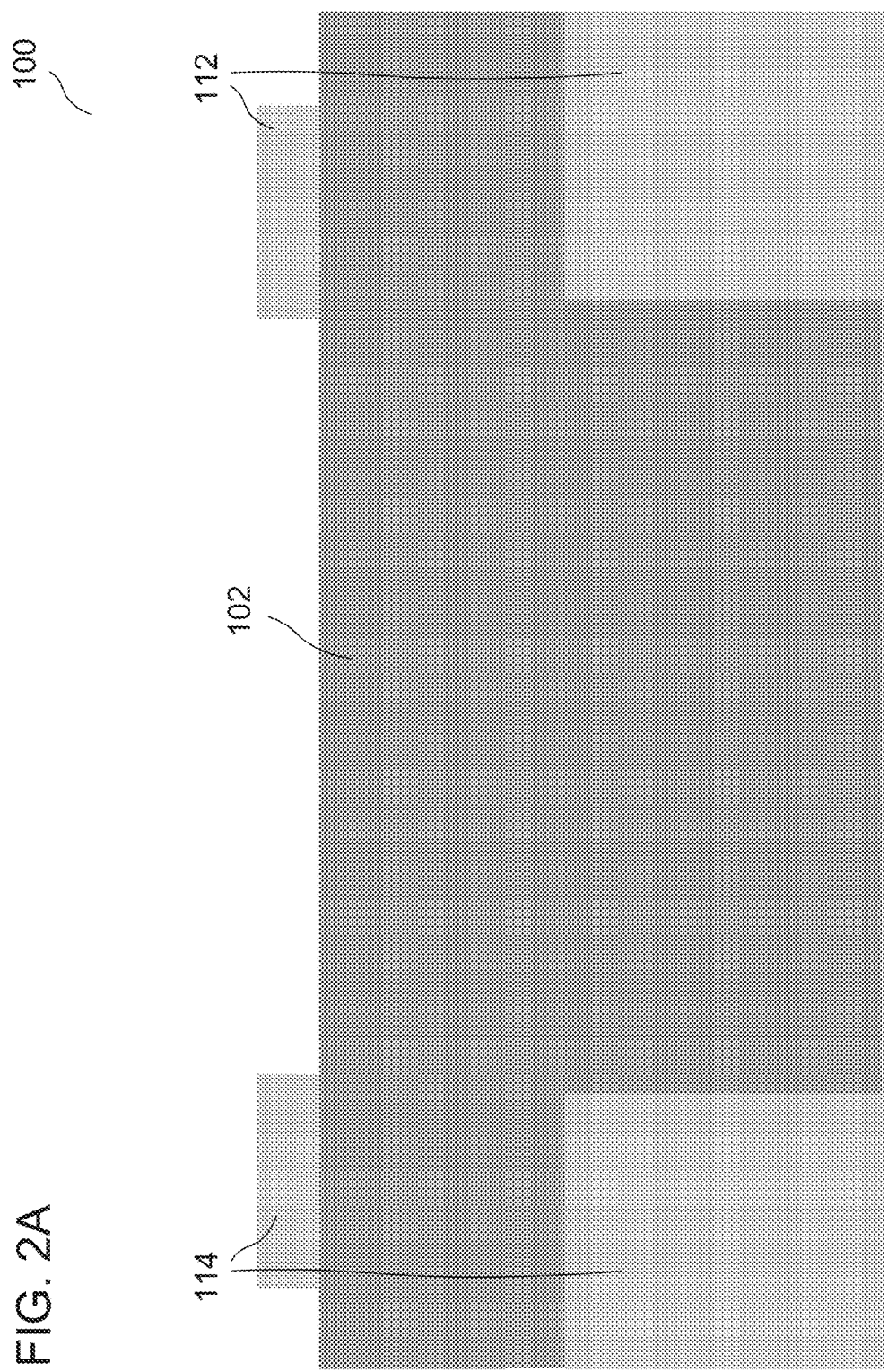

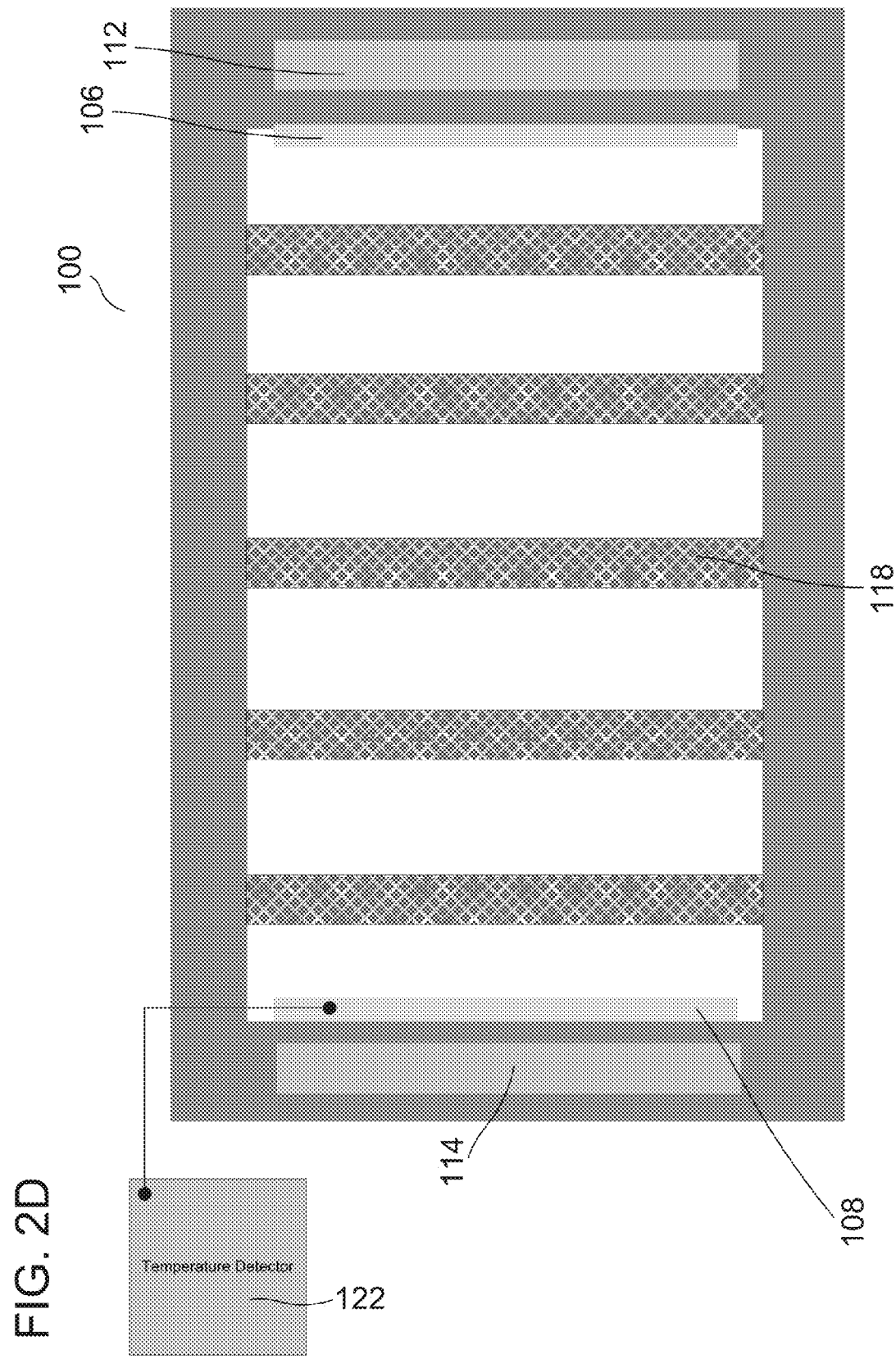

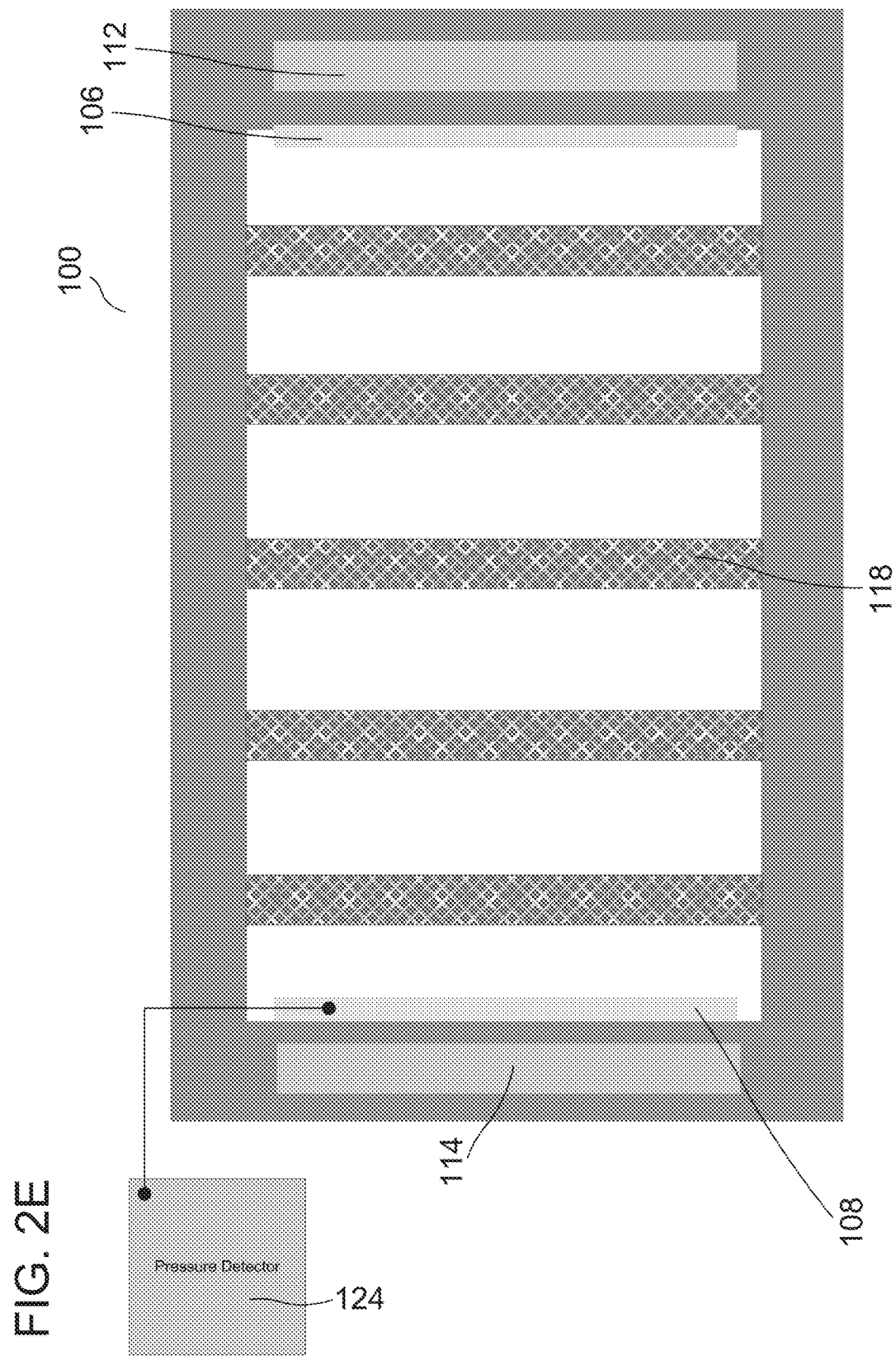

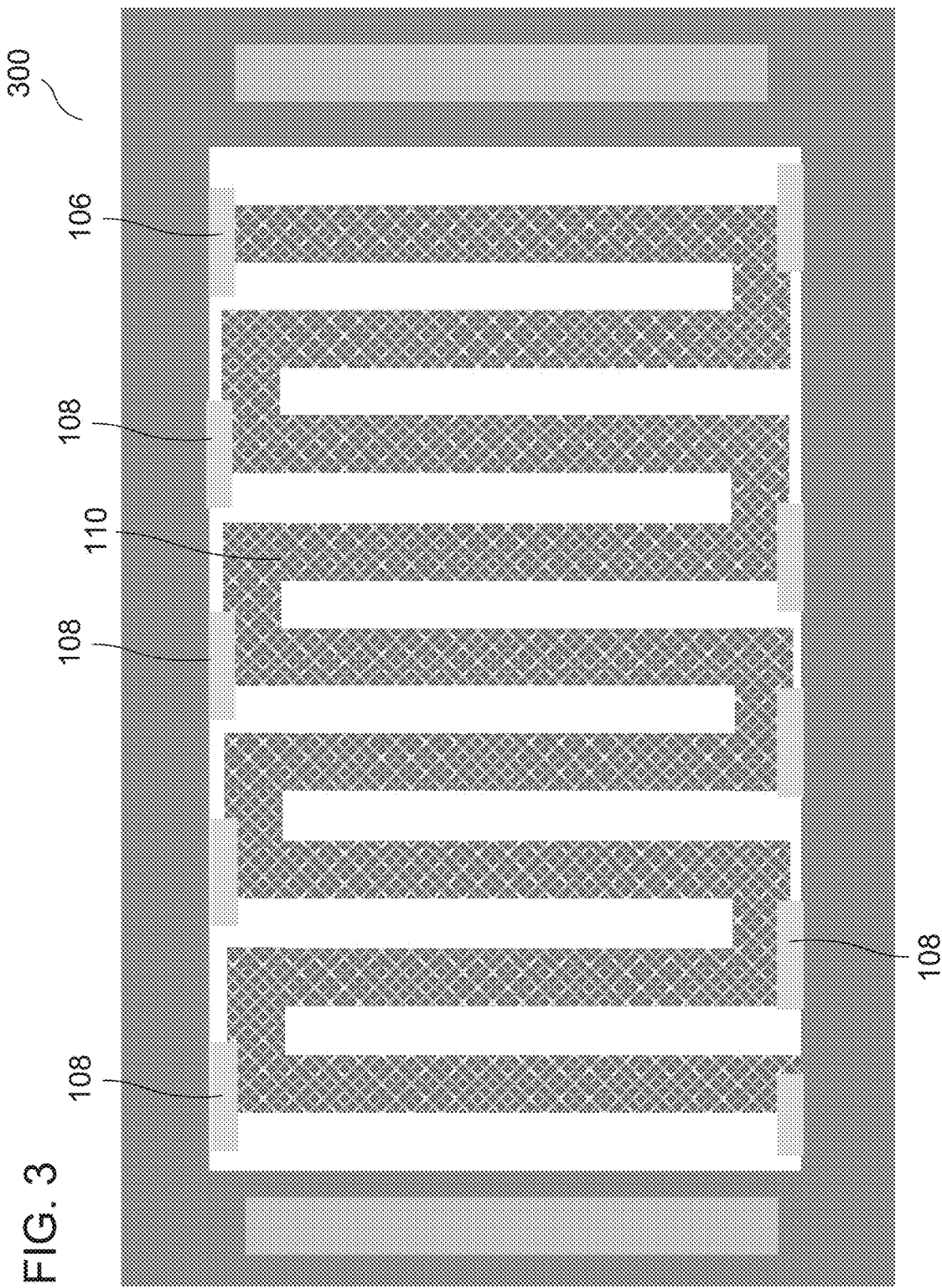

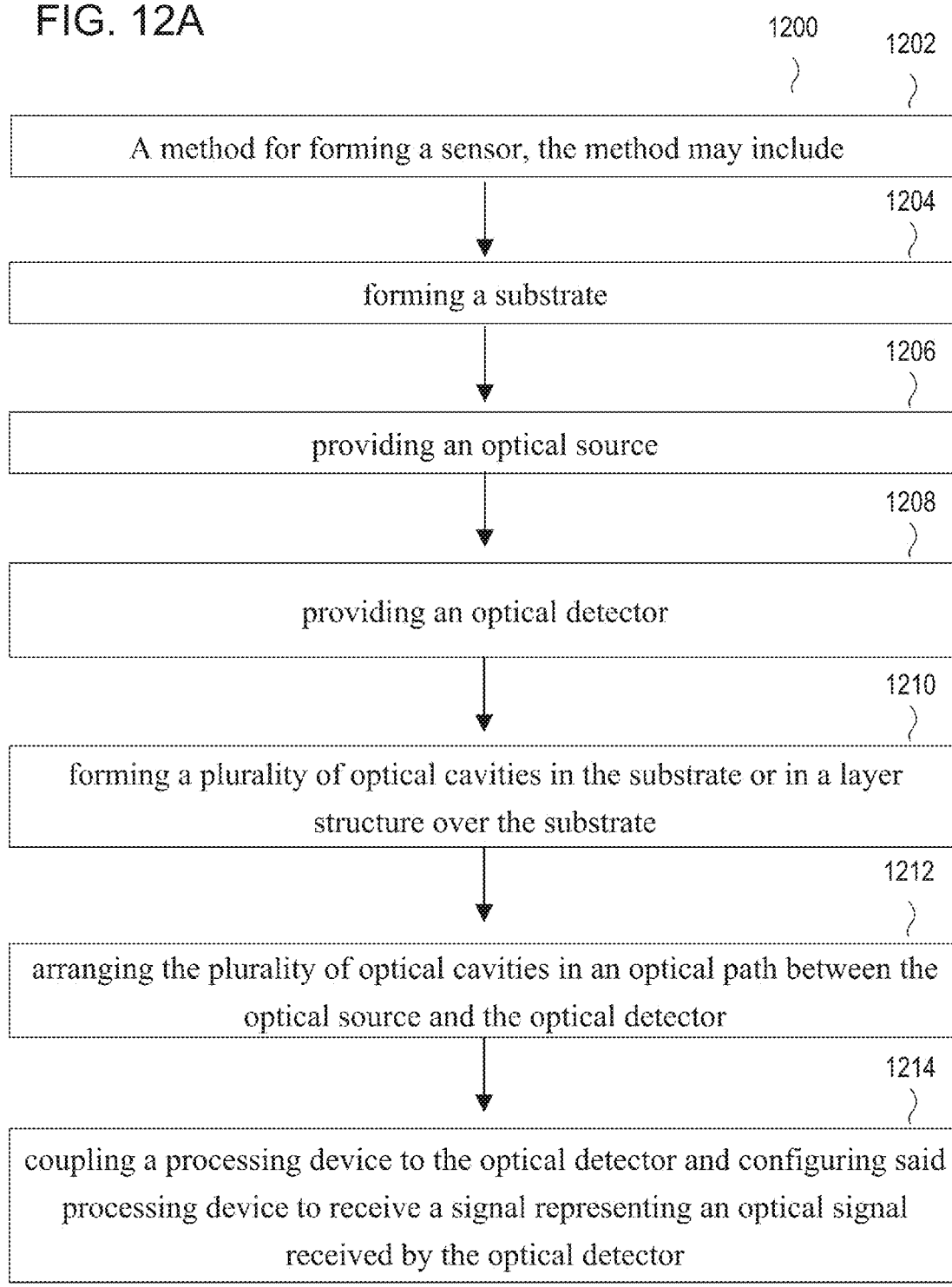

US 9,903,816 B2

PHOTONIC CRYSTAL SENSOR STRUCTURE AND A METHOD FOR MANUFACTURING THE SAME

TECHNICAL FIELD

Various embodiments relate to a sensor, which may include a photonic crystalline sensing element and method for manufacturing a sensor with a photonic crystalline sensing element.

BACKGROUND

Many sensor devices depend on a vibrating crystalline membrane in order to function. The vibration of the membrane may generate a signal which can be converted into electrical impulses. However, the membrane is stressed by this vibration. Large and/or sudden variations of ambient pressure on the membrane can cause ruptures in the membrane and consequently render the sensor inoperable. The manufacturing of a robust membrane sensor, e.g. shock resistant can be very challenging since problems in calibrating the correct elasticity (spring constant) of the membrane and, consequently, the correct operating voltage of the device often arise. A sensor and method for manufacturing the sensor, that may perform many of the same functions of a crystalline membrane sensor, but without moving parts is disclosed.

SUMMARY

In various embodiments, a sensor is provided. The sensor may include a substrate with an opening through a central portion of the substrate, an optical source in the substrate, an optical detector in the substrate, and a structure spanning the opening. According to various embodiments, a method for manufacturing a sensor is likewise disclosed.

BRIEF DESCRIPTION OF THE DRAWINGS

In the drawings, like reference characters generally refer to the same parts of the disclosure throughout the different views. The drawings are not necessarily to scale, emphasis instead generally being placed upon illustrating the principles of the disclosure. In the following description, various embodiments of the disclosure are described with reference to the following drawings, in which:

FIG. 2A shows, according to an embodiment, a sideways, cross-sectional representation of the sensor of FIG. 1;

FIG. 2D shows an overhead, planar representation of the sensor of FIG. 1, implemented as a temperature sensor, according to an embodiment;

FIG. 2E shows an overhead, planar representation of the sensor of FIG. 1, implemented as a pressure sensor according to an embodiment;

FIG. 3 shows an overhead, planar representation of the sensor of FIG. 1 where the plurality of optical cavities and the optical detector are in an alternative configuration, according to an embodiment;

FIGS. 12A & 12B illustrate in flowchart form a method of forming a sensor according to an embodiment.

DESCRIPTION

The following detailed description refers to the accompanying drawings that show, by way of illustration, specific details and embodiments in which the disclosure may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface may be used herein to mean that the deposited material may be formed "directly on", e.g. in direct contact with the implied side or surface. The word "over" used with regards to a deposited material formed "over" a side or surface may be used herein to mean that the deposited material may be formed "indirectly on" the implied side or surface with one or more additional layers being arranged between the implied side or surface and the deposited material.

The term "carrier structure" as used herein should be understood to include various structures such as, e.g. a lead frame, a semiconductor substrate, such as a silicon substrate, a printed circuit board, and/or various flexible substrates.

Figure 1:
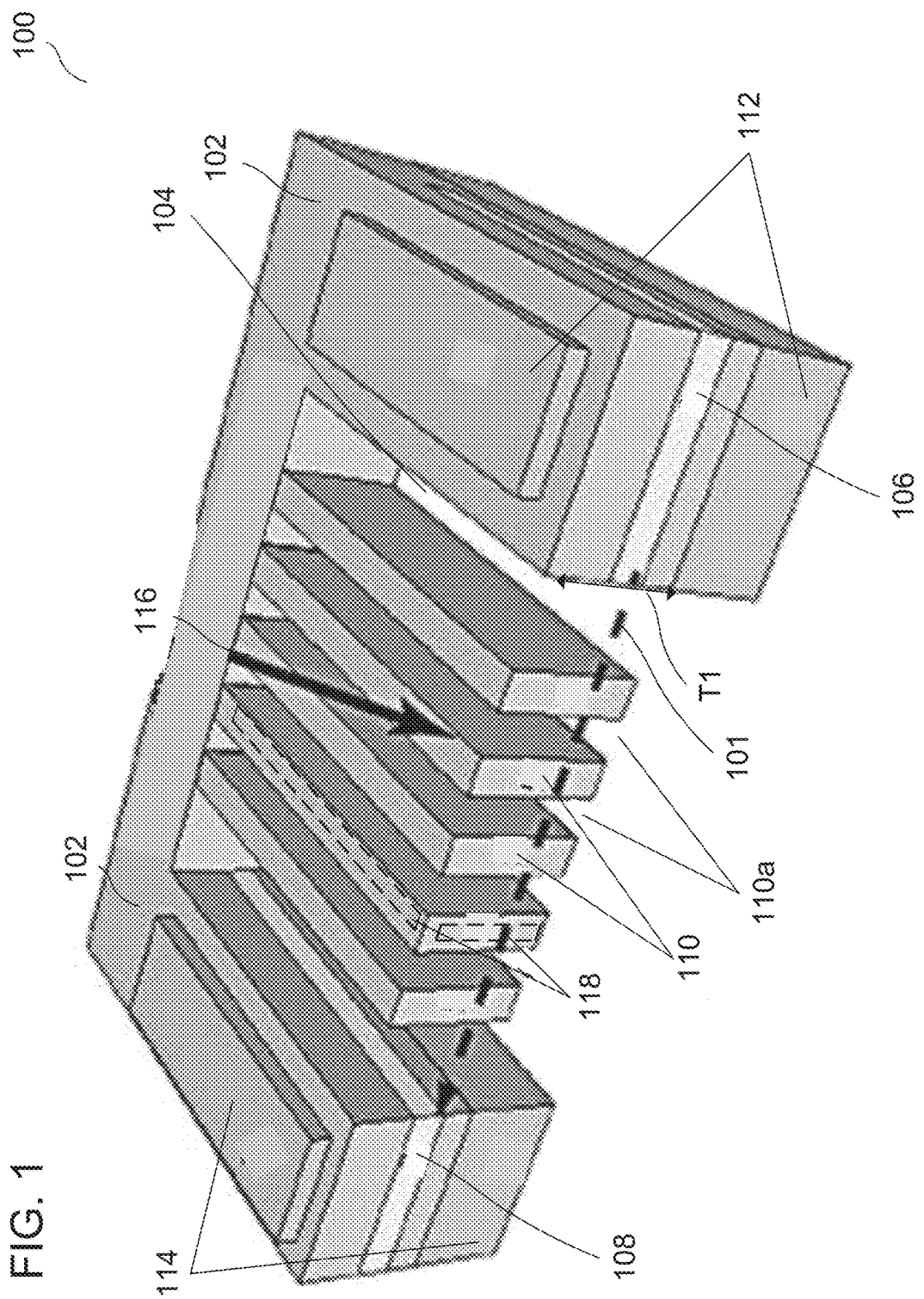
FIG. 1 shows, in accordance with a potential embodiment, a cross-sectional representation of a sensor, which may include a substrate, an optical source, an optical detector, and a plurality of optical cavities in the substrate, arranged in an optical path between the optical source and the optical detector.

According to various embodiments, as illustrated in FIG. 1, a sensor 100 is disclosed. The sensor 100, as illustrated in FIG. 1, has been divided along the dashed line 101 for ease of description and pictorial representation. The sensor 100 may include a substrate 102 and an opening 104 formed through a central portion of the substrate 102. In various embodiments, the sensor 100 may further include an optical source 106 formed in the substrate 102. According to various embodiments, the sensor 100 may further include an optical detector 108 formed in the substrate 102. In various embodiments, the sensor 100 may include a plurality of optical cavities 110 spanning the opening 104 in the substrate 102. The sensor 100 may include a first electrical element 112 which may be electrically coupled to the optical source 106. The sensor 100 may further include, in some embodiments, a second electrical element 114 which may be electrically coupled to the optical detector 108.

In various embodiments, the substrate 102 may include or essentially consist of a semiconductor material such as germanium, silicon germanium, silicon carbide, gallium nitride, indium, indium gallium nitride, indium gallium arsenide, indium gallium zinc oxide, or other elemental and/or compound semiconductors, e.g. a III-V compound semiconductor such as e.g. gallium arsenide or indium phosphide, or a II-VI compound semiconductor or a ternary compound semiconductor or a quaternary compound semiconductor, as may be desired for a given application. The substrate 102 may include or essentially consist of, for example, glass, and/or various polymers. The substrate 102 may be a silicon-on-insulator (SOI) structure. In some embodiments the substrate 102 may be a printed circuit board. According to various embodiments, the substrate 102 may be a flexible substrate, such as a flexible plastic substrate, e.g. a polyimide substrate. In various embodiments, the substrate 102 may be composed of or may include one or more of the following materials: a polyester film, a thermoset plastic, a metal, a metalized plastic, a metal foil, and a polymer. In various embodiments, the substrate 102 may be a flexible laminate structure. According to various embodiments, the substrate 102 may be a semiconductor substrate, such as a silicon substrate. The substrate 102 may include or essentially consist of other materials or combinations of material, for example various dielectrics, metals, and polymers as may be desirable for a given application. In various embodiments, the substrate 102 may have a thickness T1 in the range from about 100 µm to about 700 µm, e.g. in the range from about 150 µm to about 650 µm, e.g. in the range from about 200 µm to about 600 µm, e.g. in the range from about 250 µm to about 550 µm, e.g. in the range from about 300 µm to about 500 µm, e.g. in the range from about 350 µm to about 450 µm. In some embodiments, the substrate 102 may have a thickness T1 of at least about 100 µm, e.g. of at least 150 µm, e.g. of at least 200 µm, e.g. of at least 250 µm, e.g. of at least 300 µm. In various embodiments, the substrate 102 may have a thickness T1 of less than or equal to about 700 µm, e.g. of less than or equal to 650 µm, e.g. of less than or equal to 600 µm, e.g. of less than or equal to 550 µm, e.g. of less than or equal to 500 µm.

According to various embodiments the opening 104 may be formed in through substrate 102 using various techniques, e.g. laser drilling, various grinding techniques, deep reactive-ion etching, isotropic gas phase etching, vapor etching, wet etching, isotropic dry etching, plasma etching, various lithography techniques, etc. In various embodiments, the opening 104 may be square or substantially square in shape. The opening 104 may be rectangular or substantially rectangular in shape. According to various embodiments, the opening 104 may be a circle or substantially circular in shape. The opening 104 may be an oval or substantially oval-like in shape. According to various embodiments, the opening 104 may be a triangle or substantially triangular in shape. The opening 104 may be a cross or substantially cross shaped. According to various embodiments, the opening 104 may be formed into any shape that may be desired for a given application.

According to various embodiments, the optical source 106 may be formed in the substrate 102. The optical source 106 may be monolithically integrated with the substrate 102. In various embodiments, the optical source 106 and the substrate 102 may be formed in discrete steps and then joined and/or coupled together using various means. The optical source 106 and the substrate 102 may be implemented as a type of laminate structure. According to various embodiments, the optical source 106 may be formed in the substrate 102 through various techniques, e.g. vapor deposition, an electrochemical process, and electroplating process, an electroless process, a chemical vapor deposition process, molecular beam epitaxy, spin coating, a sputter deposition, and/or various other techniques as may be desirable for a given application. In various embodiments, the optical source 106 may be implemented as a type of light emitting diode (LED). In various other embodiments, the optical source 106 may be implemented as a light emitting semiconductor wafer, such as a semiconductor laser. In various embodiments, the optical source 106 may be implemented as a hybrid silicon laser. In some embodiments, the optical source 106 may be implemented as any light emitting means desirable for a given application. In some embodiments, the optical source 106 can be an external light source. The optical source 106 may include or essentially consist of a semiconductor material such as germanium, silicon germanium, silicon carbide, gallium nitride, indium, indium gallium nitride, indium gallium arsenide, indium gallium zinc oxide, or other elemental and/or compound semiconductors, e.g. a III-V compound semiconductor such as e.g. gallium arsenide or indium phosphide, or a II-VI compound semiconductor or a ternary compound semiconductor or a quaternary compound semiconductor, as may be desired for a given application. The optical source 106 may include or essentially consist of, for example, glass, and/or various polymers. The optical source 106 may be a silicon-on-insulator (SOI) structure. The optical source 106 may include or essentially consist of other materials or combinations of material, for example various dielectrics, metals, and polymers as may be desirable for a given application.

According to various embodiments, the optical detector 108 may be formed in the substrate 102. The optical detector 108 may be monolithically integrated with the substrate 102. In various embodiments, the optical detector 108 and the substrate 102 may be formed in discrete steps and then joined and/or coupled together using various means. The optical detector 108 and the substrate 102 may be implemented as a type of laminate structure. According to various embodiments, the optical detector 108 may be formed in the substrate 102 through various techniques, e.g. vapor deposition, an electrochemical process, and electroplating process, an electroless process, a chemical vapor deposition process, molecular beam epitaxy, spin coating, a sputter deposition, and/or various other techniques as may be desirable for a given application. In various embodiments, the optical detector 108 may be implemented as a type of light emitting diode (LED). In various other embodiments, the optical detector 108 may be implemented as a type of photodetector, such as a photodiode and/or a type of phototransistor. In at least one embodiment, the optical detector 108 is implemented as at least two photodetector 108 configured to measure an amount of light transmitted through the plurality of optical cavities 110 and an amount of light reflected by the plurality of optical cavities 110. In embodiments, with more than one optical detector 108, the amount of light reflected by the plurality of optical cavities 110 and the amount transmitted by the plurality of optical cavities 110 may be compared and/or analyzed with the mathematical relation light transmitted+light reflected=1. In other words, the difference in the amounts of light transmitted and reflected may be analyzed and/or utilized to detect a change in one or more properties of the light emitted by the optical source 106. In some embodiments, the optical detector 108 may be implemented as any light detecting means desirable for a given application. In some embodiments, the optical detector 108 can be implemented as an external optical detector, e.g. a detector not integrated into the substrate 102. The optical detector 108 may include or essentially consist of a semiconductor material such as germanium, silicon germanium, silicon carbide, gallium nitride, indium, indium gallium nitride, indium gallium arsenide, indium gallium zinc oxide, or other elemental and/or compound semiconductors, e.g. a III-V compound semiconductor such as e.g. gallium arsenide or indium phosphide, or a II-VI compound semiconductor or a ternary compound semiconductor or a quaternary compound semiconductor, as may be desired for a given application. The optical detector 108 may include or essentially consist of, for example, glass, and/or various polymers. The optical detector 108 may be a silicon-on-insulator (SOI) structure. The optical detector may include or essentially consist of other materials or combinations of material, for example various dielectrics, metals, and polymers as may be desirable for a given application.

According to various embodiments, the plurality of optical cavities 110 spanning the opening 104 in the substrate 102 may be implemented as a semiconductor structure, e.g. the plurality of optical cavities 110 include or essentially consist of a semiconductor material such as germanium, silicon germanium, silicon carbide, gallium nitride, indium, indium gallium nitride, indium gallium arsenide, indium gallium zinc oxide, or other elemental and/or compound semiconductors, e.g. a III-V compound semiconductor such as e.g. gallium arsenide or indium phosphide, or a II-VI compound semiconductor or a ternary compound semiconductor or a quaternary compound semiconductor, as may be desired for a given application. In some embodiments, the plurality of optical cavities 110 may be implemented as a type of crystalline structure, such as a photonic crystalline structure. The plurality of optical cavities 110 may be implemented and/or may include a one-dimensional photonic crystalline structure. In other embodiments, the plurality of optical cavities 110 may be implemented and/or may include a two-dimensional photonic crystalline. According to an embodiment, the plurality of optical cavities 110 may be implemented and/or may include a three-dimensional photonic crystalline structure. In further embodiments, the plurality of optical cavities 110 may be implemented and/or may include a variety of one-dimensional, two-dimensional, and/or three dimensional photonic crystalline structures. In various embodiments, the plurality of optical cavities 110 may include or essentially consist of other materials or combinations of material, for example various dielectrics, metals, and polymers as may be desirable for a given application. In some embodiment, the plurality of optical cavities 110 may be implemented as a plurality of structures which partition and/or divide the opening 104 into a plurality of openings.

According to various embodiments, the first electrical element 112 may be impended as a first pair of contact pads 112 formed on the substrate 102. In various embodiments, the first pair of contact pads 112 may be electrically coupled to the optical source 106. The first pair of contact pads 112 may be capable of receiving and/or transmitting an electromagnetic signal to and/or from the optical source 106. In some embodiments, the first pair of contact pads 112 may be configured to relay electrical energy to the optical source 106, e.g. in embodiments where the optical source may be implemented as an LED, the first pair of contact pads 112 may be used to supply electrical power to the LED. In some embodiments the first pair of contact pads 112 may be formed over opposing surfaces of the substrate 102. The first pair of contact pads 112 may be arranged in a stack-like layered structure with the substrate 102 and the optical source 106 arranged between the first pair of contact pads 112. In some embodiments, the first pair of contact pads 112 may be formed over the same surface of the substrate 102. According to various embodiments, the first pair of contact pads 112 may be deposited through various techniques, e.g. vapor deposition, an electrochemical process, and electroplating process, an electroless process, a chemical vapor deposition process, molecular beam epitaxy, spin coating, a sputter deposition, and/or various other techniques as may be desirable for a given application. In various embodiments, the first pair of contact pads 112 may be formed of a conductive material such as a metallic material, a metalized material, a metal foil, an elemental metal, and/or a metal alloy. For example, the first pair of contact pads 112 may include or essentially consist of copper, nickel, tin, lead, silver, gold, aluminum, titanium, gallium, indium, boron, and various alloys of these materials such as e.g. cupronickel, nickel-aluminum, aluminum-copper-silicon, etc. Further, the first pair of contact pads 112 may include or essentially consist of other materials as may be desirable for a given application.

According to various embodiments, the second electrical element 114 may be impended as a second pair of contact pads 114 formed on the substrate 102. In various embodiments, the second pair of contact pads 114 may be electrically coupled to the optical detector 108. The second pair of contact pads 114 may be capable of receiving and/or transmitting an electro-magnetic signal to and/or from the optical detector 108. In some embodiments, the second pair of contact pads 114 may be configured to relay electrical energy from the optical source 108, e.g. in embodiments where the optical source may be implemented as a photodetector, the second pair of contact pads 114 may be used relay signals received by the photodetector to various processing circuity (not shown). In some embodiments the second pair of contact pads 114 may be formed over opposing surfaces of the substrate 102. The second pair of contact pads 114 may be arranged in a stack-like layered structure with the substrate 102 and the optical detector 108 arranged between the second pair of contact pads 114. In some embodiments, the second pair of contact pads 114 may be formed over the same surface of the substrate 102. According to various embodiments, the second pair of contact pads 114 may be deposited through various techniques, e.g. vapor deposition, an electrochemical process, and electroplating process, an electroless process, a chemical vapor deposition process, molecular beam epitaxy, spin coating, a sputter deposition, and/or various other techniques as may be desirable for a given application. In various embodiments, the second pair of contact pads 114 may be formed of a conductive material such as a metallic material, a metalized material, a metal foil, an elemental metal, and/or a metal alloy. For example, the second pair of contact pads 114 may include or essentially consist of copper, nickel, tin, lead, silver, gold, aluminum, titanium, gallium, indium, boron, and various alloys of these materials such as e.g. cupronickel, nickel-aluminum, aluminum-copper-silicon, etc. Further, the second pair of contact pads 114 may include or essentially consist of other materials as may be desirable for a given application.

According to various embodiments, the plurality of optical cavities 110 may be implemented to include a plurality of openings and/or spaces 110a. In such embodiments, a pressure wave 116 which may be incident on the plurality of optical cavities 110 may pass through the plurality of openings 110a. In some embodiments, the pressure wave may cause a deformation and or deflection of at least one surface of the structure(s) 110. In some embodiments the pressure wave 116 may change the refractive index of the structure(s) 110. In various embodiments, the structure(s) 110 may contain a cavity 118.

According to various embodiments, the cavity 118 may be formed in the plurality of optical cavities 110 through various techniques, e.g. laser drilling. While in various other embodiments, the cavity 118 may be formed in the structure during the manufacturing process of the plurality of optical cavities 110. In various embodiments, the cavity 118 may be essentially the same shape as the plurality of optical cavities 110 and may be formed along an axis of the plurality of optical cavities 110. In some embodiments, the cavity 118 may be capable of sustaining an ambient pressure which may be higher than the ambient pressure outside the cavity 118. According to an embodiment, the pressure in the cavity 118 may be in the range from about 100 kPa to about 800 kPa, e.g. in the range from about 100 kPa to about 125 kPa, e.g. in the range from about 125 kPa to about 150 kPa, e.g. in the range from about 150 kPa to about 175 kPa, e.g. in the range from about 175 kPa to about 200 kPa, e.g. in the range from about 200 kPa to about 350 kPa, e.g. in the range from about 350 kPa to about 500 kPa, e.g. in the range from about 500 kPa to about 800 kPa.

Figure 2B:
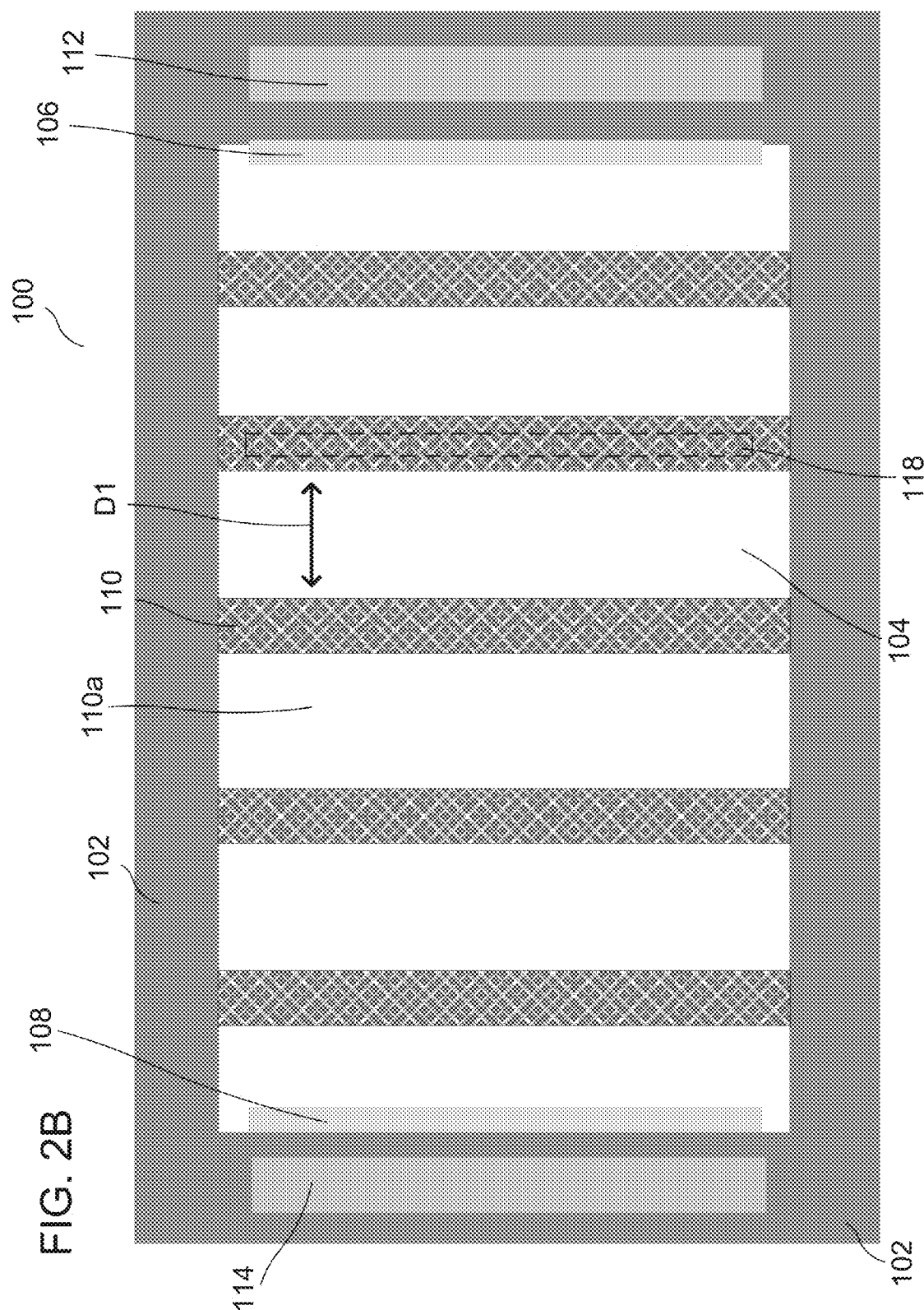
FIG. 2B shows an overhead, planar representation of the sensor of FIG. 1, according to an embodiment.

According to various embodiments, as shown in FIGS. 2A & 2B, the first pair of contact pads 112 and the second pair of contact pads 114 may be arranged at opposing ends of the sensor 100. In some embodiments, as shown in FIGS. 2A & 2B, the optical source 106 and the optical source 108 may be at least partially enclosed by the substrate 102. The plurality of optical cavities 110 may be square or substantially square in shape. According to various embodiments, the plurality of optical cavities 110 may be rectangular or substantially rectangular in shape. According to various embodiments, the plurality of optical cavities 110 may be a circle or substantially circular in shape. According to various embodiments, the plurality of optical cavities 110 may be an oval or substantially oval in shape. According to various embodiments, the plurality of optical cavities 110 may be a triangle or substantially triangular in shape. According to various embodiments, the plurality of optical cavities 110 may be a cross or substantially cross shaped. The plurality of optical cavities 110 may be formed into any shape that may be desired for a given application. In some embodiments, the plurality of optical cavities 110 may be implemented as a plurality of optical cavities 110. In embodiments where the plurality of optical cavities 110 may be implemented as a plurality of optical cavities 110, the plurality of optical cavities 110 may be separated from one another by openings 110a. In some embodiments, the plurality of optical cavities 110 may be implemented to include a number of optical cavities 110, e.g. in the range from about 400 to about 1200, e.g. in the range from about 400 optical cavities to about 500 optical cavities, e.g. in the range from about 500 to about 600, e.g. in the range from about 600 to about 700, from about 700 to about 800, from about 800 to about 1000, from about 1000 to about 1200. According to various embodiments, the distance, D1, between the plurality of optical cavities 110 may be in the range from about 1 µm to about 10 µm; e.g. in the range from about 1 µm to about 1.5 µm; e.g. in the range from about 1.5 µm to about 3 µm; e.g. in the range from about 3 µm to about 5 µm; e.g. in the range from about 5 µm to about 7.5 µm; e.g. in the range from about 7.5 µm to about 9 µm; e.g. in the range from about 9 µm to about 10 µm. In some embodiments, the openings 110a may be square or substantially square in shape. According to various embodiments, the openings 110a may be rectangular or substantially rectangular in shape. According to various embodiments, the openings 110a may be a circle or substantially circular in shape. According to various embodiments, the openings 110a may be an oval or substantially oval in shape. According to various embodiments, the openings 110a may be a triangle or substantially triangular in shape. According to various embodiments, the openings 110a may be a cross or substantially cross shaped. The openings 110a may be formed into any shape that may be desired for a given application. In some embodiments, the optical source 106 and the optical detector 108 may be located on opposing ends of the opening 104. The optical source 106 may be located in the substrate 104 such that a portion of the light emitted by the optical source 106 may pass through the plurality of optical cavities 110 and be detected by the optical detector 108.

Figure 2C:
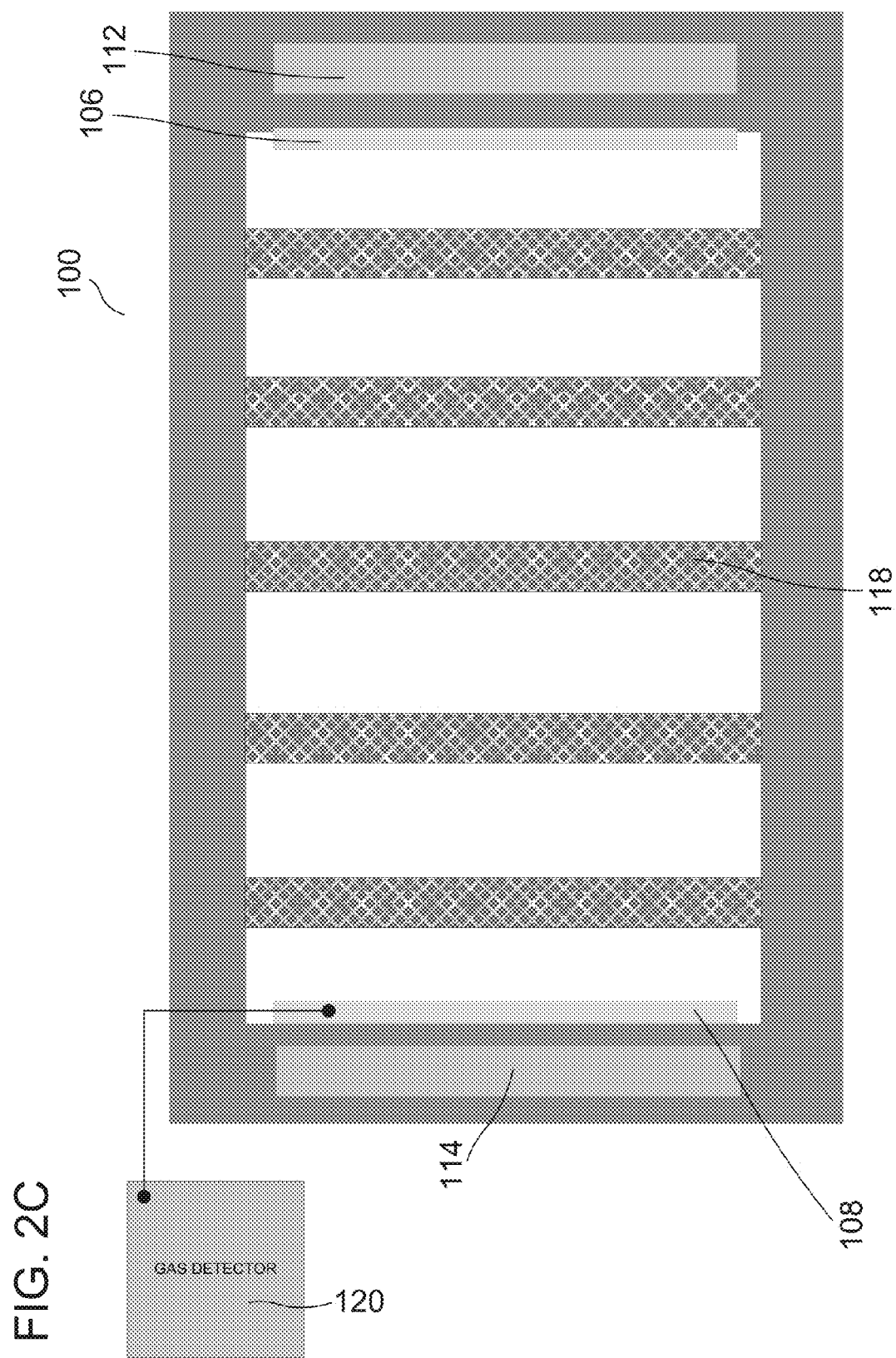
FIG. 2C shows an overhead, planar representation of the sensor of FIG. 1, implemented as a gas detection sensor, according to an embodiment.

In various embodiments, as illustrated in FIG. 2C, the sensor 100 may be implemented as a gas sensor. The sensor 100, when implemented as a gas sensor, may include a gas detector 120. The gas detector 120 may be coupled to the optical detector 108. In some embodiments, the gas detector 120 may be configured to receive a signal representing an optical signal received by the optical detector 108 and to determine if one or more predefined gases are present in the plurality of optical cavities 118 based on the received signal. In various embodiments, the gas detector 120 may be implemented as various types of infrared gas detectors, e.g. an infrared point gas detector and/or a passive or active infrared imaging detector. The gas detector 120 may be implemented as a type of holographic gas detector. The gas detector 120 may be implemented as any type of gas detector desirable for a given application.

In various embodiments, as illustrated in FIG. 2D, the sensor 100 may be implemented as a temperature sensor. The sensor 100, when implemented as a temperature sensor, may include a temperature detector 122. The temperature detector 122 may be coupled to the optical detector 108. In some embodiments, the temperature detector 122 may be configured to receive a signal representing an optical signal received by the optical detector 108 and to determine a temperature, based on the received signal. In various embodiments, the temperature detector 122 may be implemented as various types of temperature detecting devices, e.g. a silicon band-gap temperature sensor. In at least one embodiment, the temperature detector 122 may be an integrated circuit capable extrapolating an ambient temperature based on a changes to a beam of light generated in the optical source 106, passed through the optical cavities 118, and received by the optical detector 108. The optical cavities 118 may alter the characteristics of the light beam in a temperature dependent fashion, e.g. a change in refractive index.

In various embodiments, as illustrated in FIG. 2E, the sensor 100 may be implemented as a pressure sensor. The sensor 100, when implemented as a pressure sensor, may include a pressure detector 124. The pressure detector 124 may be coupled to the optical detector 108. In some embodiments, the pressure detector 124 may be configured to receive a signal representing an optical signal received by the optical detector 108 and to determine and/or sense a change in ambient pressure based on the received signal. In various embodiments, the pressure detector 124 may be implemented as various types of integrated circuit capable extrapolating an ambient pressure, or change therein, based on a changes to a beam of light generated in the optical source 106, passed through the optical cavities 118, and received by the optical detector 108. In various embodiments, the optical cavities 118 may alter and/or change shape as a result of a change in the ambient pressure, i.e. at least one surface of the optical cavities 118 may deflect due to the change in pressure. In some embodiments, this deflection may alter the characteristics of the light beam, e.g. a change in intensity.

According to various embodiments, as illustrated in FIG. 3, the plurality of optical cavities 110 may be implemented as a substantially square-wave shaped structure, several sections of which may span the opening 104. In some embodiments the optical source 106 may be formed at a first end of such a plurality of optical cavities 110 and the optical detector 108 may be implemented as several optical detectors. In various embodiments where the optical detector 108 may be implemented as several optical detectors 108, each of the optical detectors 108 may be located along the perimeter of the opening 104. In embodiments where the plurality of optical cavities 110 is implemented as a substantially square-wave shaped structure, an optical detector 108 may be located at any or all of the corners of the plurality of optical cavities 110.

Figure 4:
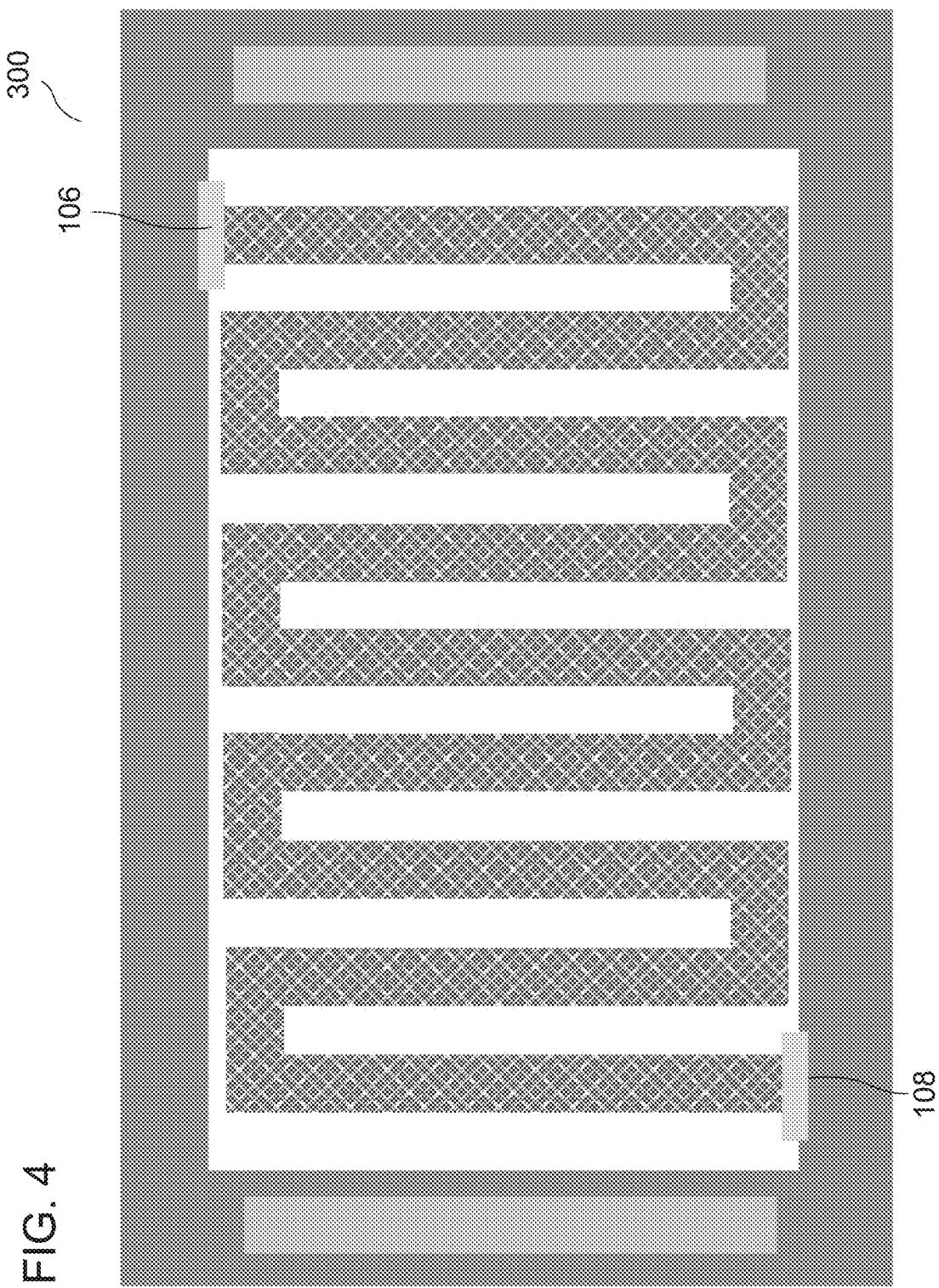
FIG. 4 shows an overhead, planar representation of the sensor of FIG. 3 where the plurality of optical cavities and the optical detector are in an alternative configuration, according to an embodiment.

According to various embodiments, as illustrated in FIG. 4, where the plurality of optical cavities 110 may be implemented as a substantially square-wave shaped structure, the optical source 106 may be located and/or coupled to a first end of the plurality of optical cavities 110 and the optical detector 108 may be located and or coupled at the opposite end of the plurality of optical cavities 110. In various embodiments, the structure may be configured to channel and/or direct a light impulse(s) from the optical source 106 to the optical detector 108.

Figure 5:
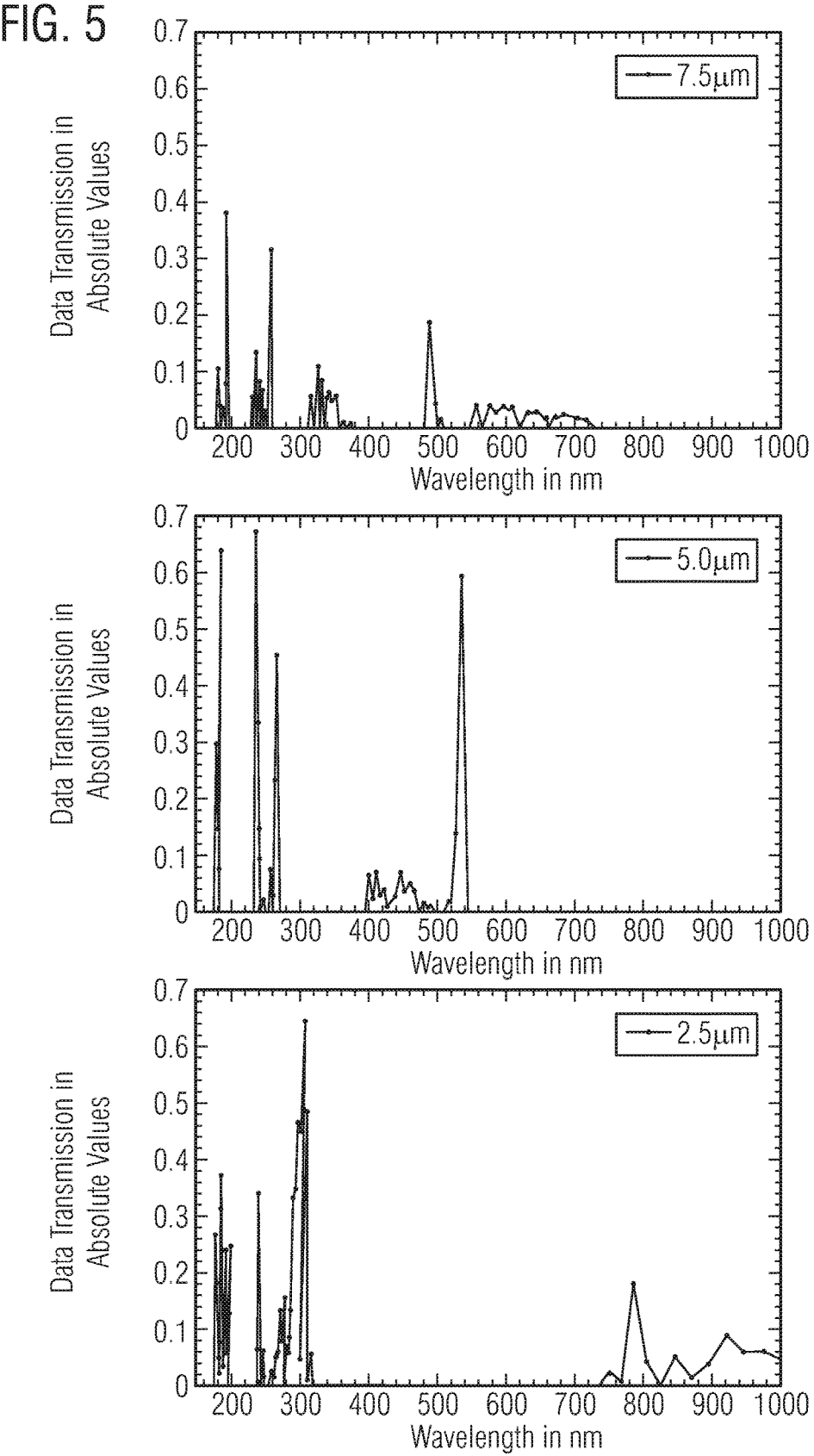
FIGS. 5-11 depict graphical representations of theoretical calculation data for embodiments of the disclosed sensor.

According to various embodiments, and as illustrated graphically by FIG. 5, the amount of light transmitted by the plurality of optical cavities 110 may vary based on several factors, e.g. the pressure inside the cavity 118, the number of optical cavities 110 and or openings 110a, and/or the distance, D1, between the optical cavities 110.

Figure 6:
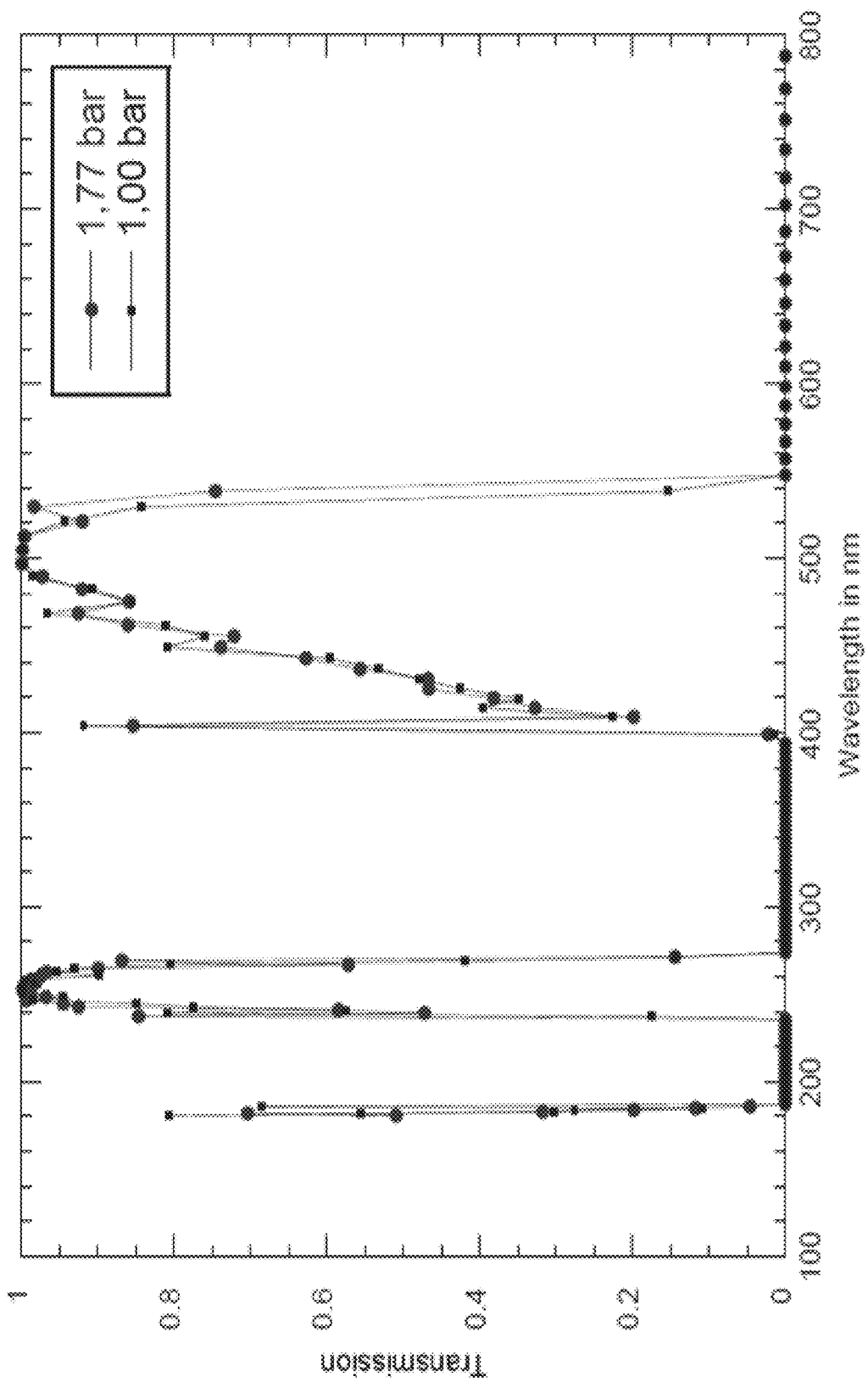

In FIG. 6, the result of light transmission calculations through the plurality of optical cavities 110 as a function of wave length is depicted. The exemplary embodiment used to obtain the results of FIG. 6 included eight hundred openings 110a and was tested with two pressures in the cavity 118.

Figure 7:
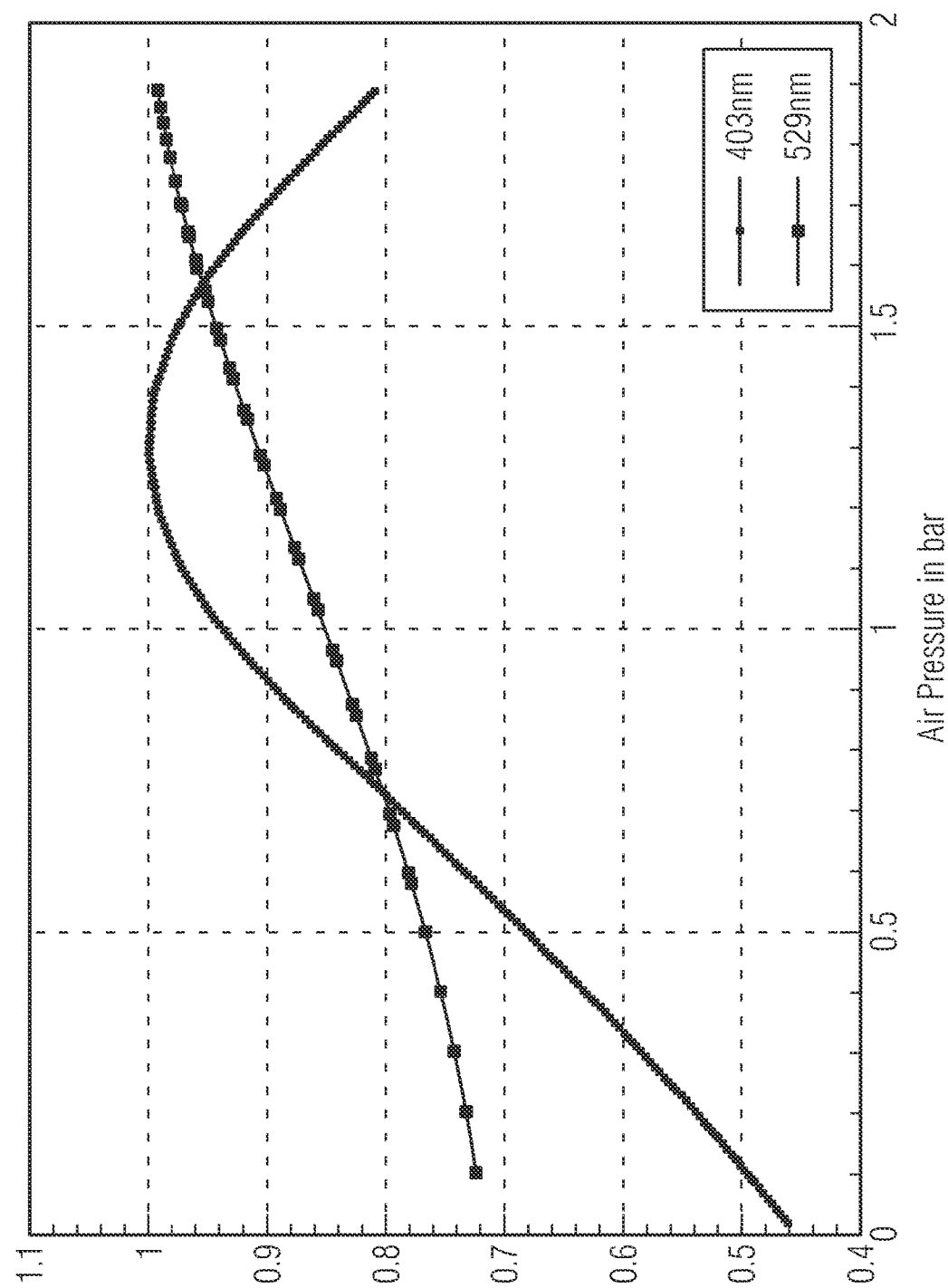

In FIG. 7, according to an embodiment, the transmission of light through the plurality of optical cavities 110 as a function of pressure is depicted. The particular embodiment used to obtain the results depicted in FIG. 7 included eight hundred openings 110a. Further, as represented in FIG. 7, two different wavelengths of light were likewise used to obtain the data.

Figure 8:
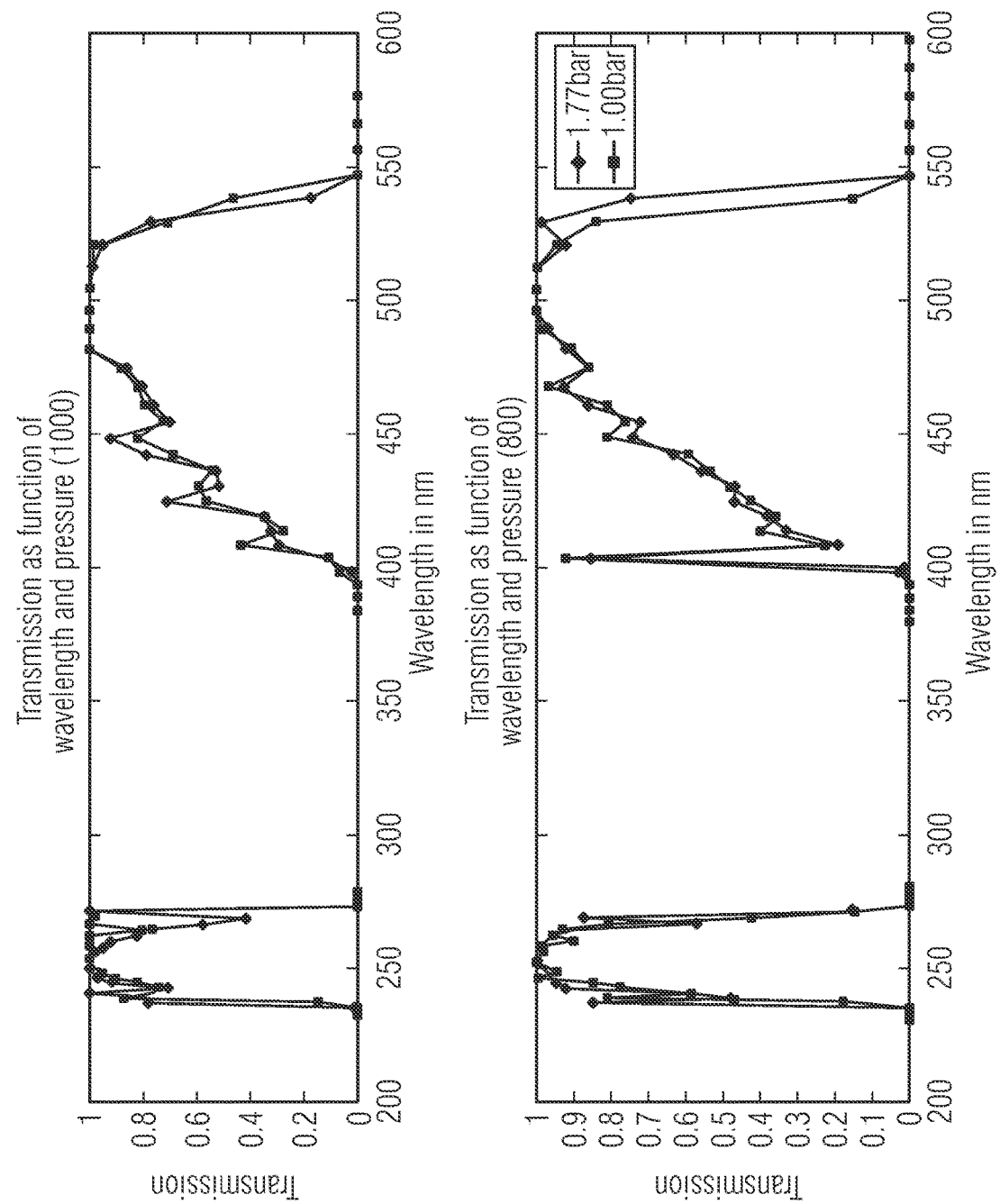

According to various embodiments, as depicted in FIG. 8, both the wave length of the light emitted by the optical source 106 and the pressure inside the cavity 118 may change and/or alter the light transmitted by the plurality of optical cavities 110 to the optical detector 108. The particular embodiment used to obtain the results depicted in FIG. 8 included eight hundred openings 110a.

Figure 9:
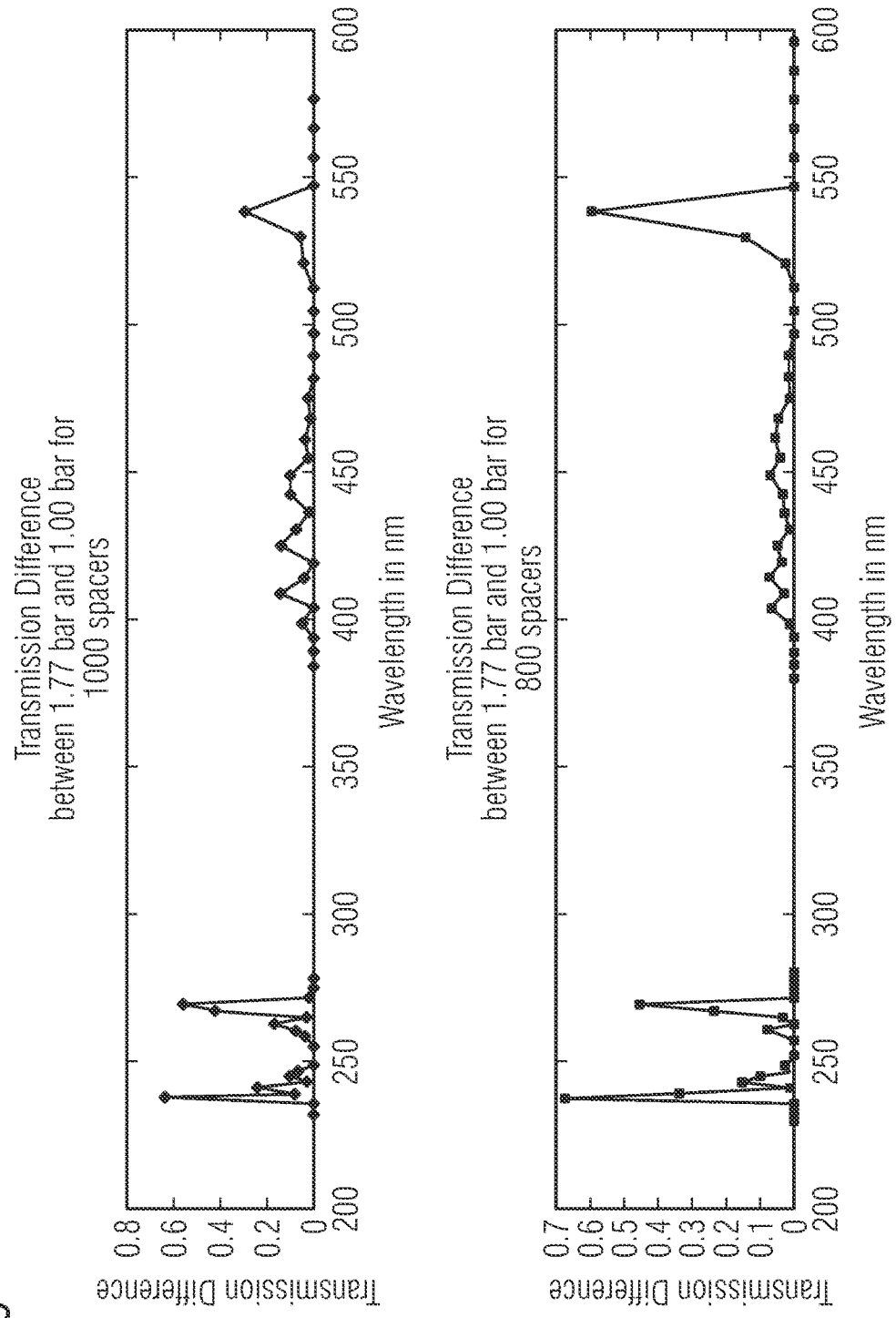

In various embodiments, the results of theoretical models and/or calculations are reflected by the charts of FIG. 9, the chart display the difference in light transmitted at differing pressures through one thousand openings 110a.

Figure 10:
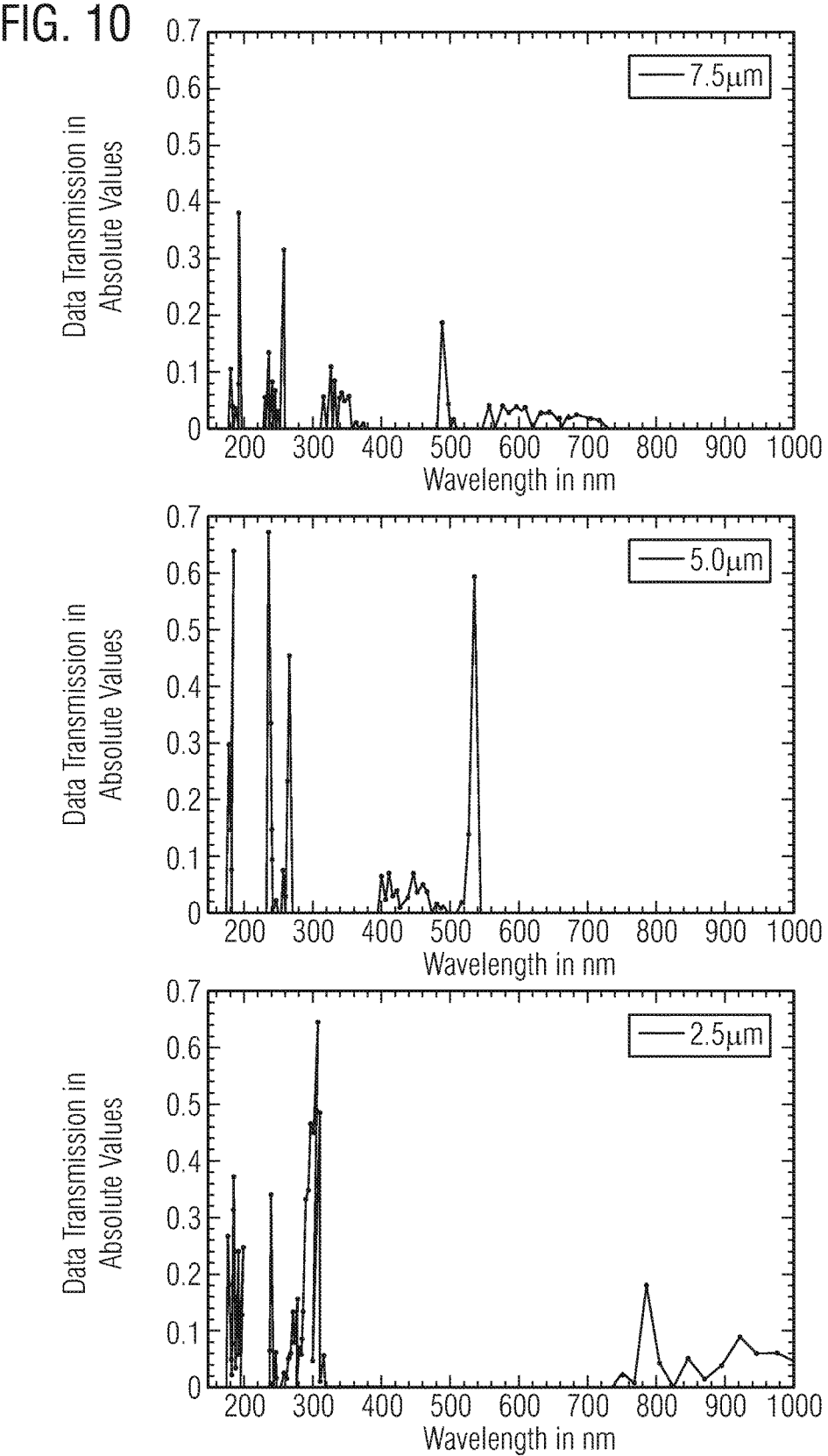
Figure 11:
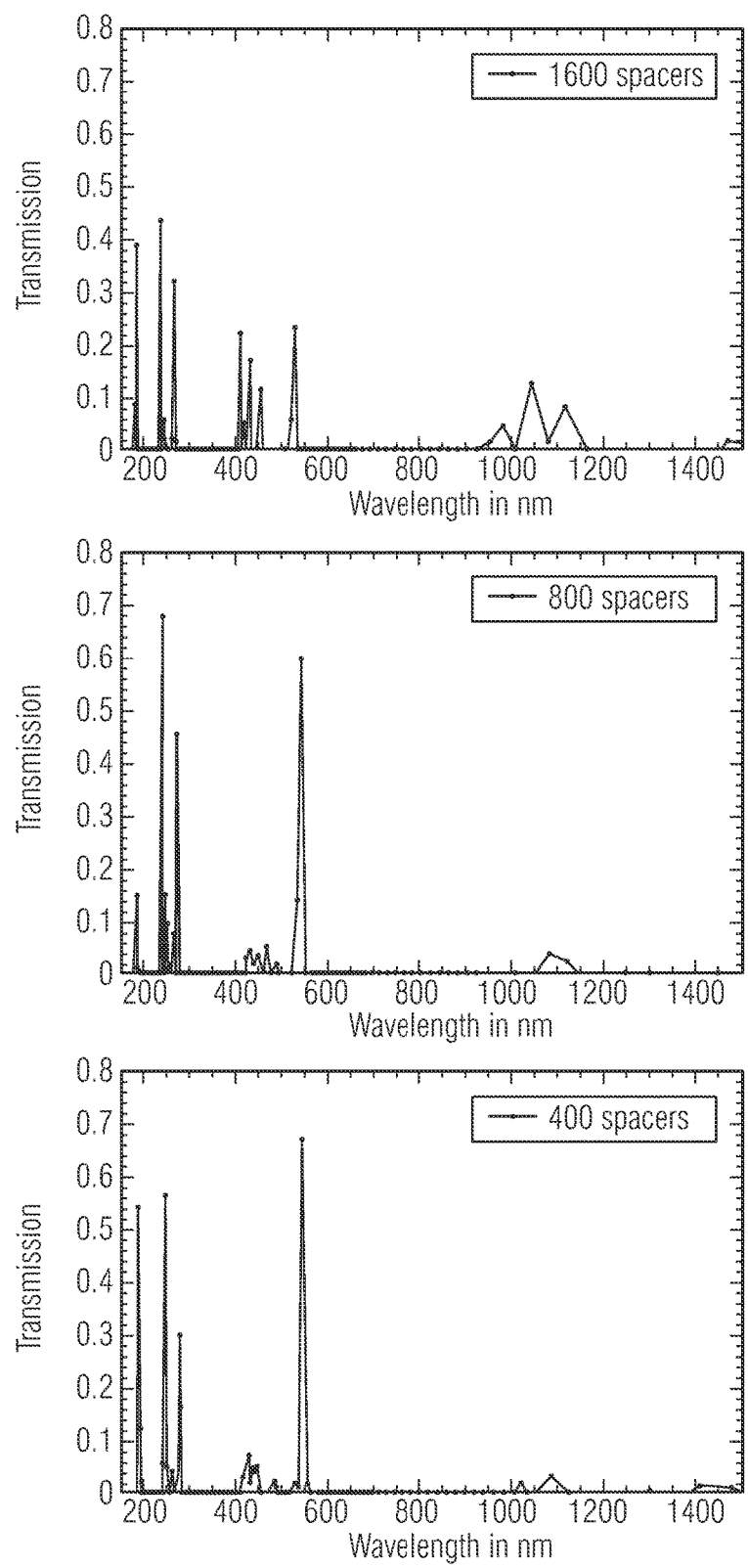

According to various embodiments, FIGS. 10 & 11 depict theoretical results and/or calculation models, similar to those depicted in FIGS. 5-9 and differ manly in the size and/or number of the gaps 11a.

Figure 12B:
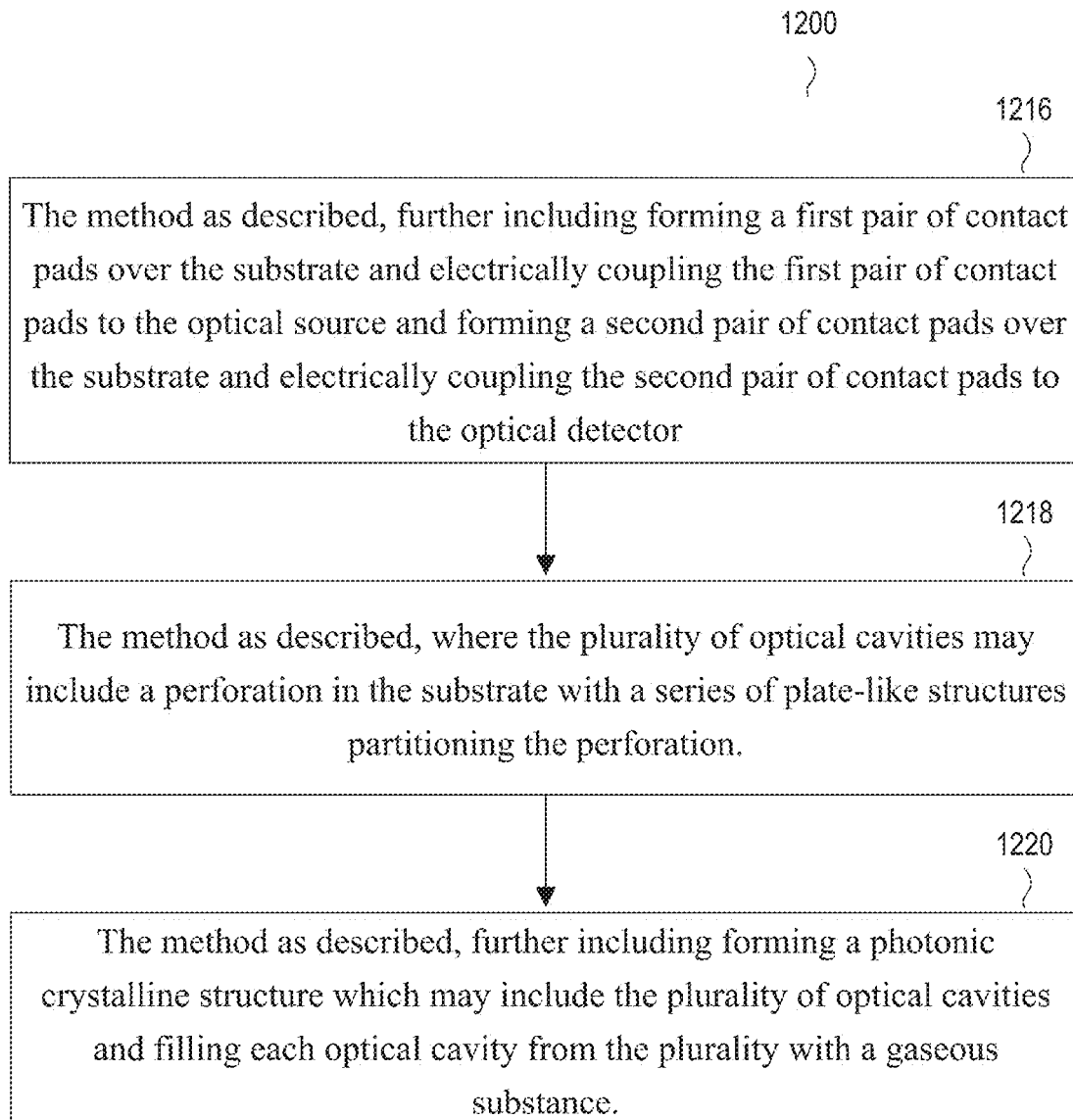

According to various embodiments, and as depicted in FIGS. 12A & 12B, a method 1200 for forming a transducer structure is disclosed. The method 1200 may include, as depicted in 1202, the following steps, forming as substrate, as disclosed in 1204. According to various embodiments, the method 1200 may further include, as shown in 1206, providing an optical source. The method 1200 may further include, as shown in 1208, providing an optical detector. According to various embodiments, the method 1200 may include, as shown in 1210, forming a plurality of optical cavities in the substrate or in a layer structure over the substrate. As shown in 1212, the method 1200 may include arranging the plurality of optical cavities in an optical path between the optical source and the optical detector. In some embodiments, the method 1200 may include, as shown in 1214, coupling a processing device to the optical detector and configuring said processing device to receive a signal representing an optical signal received by the optical detector. The method 1200 may further include forming a first pair of contact pads over the substrate and electrically coupling the first pair of contact pads to the optical source and forming a second pair of contact pads over the substrate and coupling the second pair of contact pads to the optical detector as shown in 1216. In some embodiments, as shown in 1218, the method 1200 where the plurality of optical cavities may include a perforation in the substrate with a series of plate-like structure partitioning the perforation. According to an embodiment, the method 1200 may further include forming a photonic crystalline structure which may include the plurality of optical cavities and filling each optical cavity from the plurality with a gaseous substance, as depicted in 1220. In at least one embodiment, the method 1200 may further include filling each optical cavity from the plurality with a fluid and/or a mixture of fluids.

The following examples pertain to further embodiments.

In Example 1, a gas sensor, which may include a substrate, an optical source, an optical detector, a plurality of optical cavities in the substrate or in a layer structure over the substrate; where the plurality of optical cavities may be arranged in an optical path between the optical source and the optical detector; and a gas detector coupled to the optical detector and configured to receive a signal representing an optical signal received by the optical detector and to determine if one or more predefined gases are present in the plurality of optical cavities based on the received signal.

In Example 2, the gas sensor of Example 1, where the optical source may be configured to generate an optical source signal transmitted to the optical detector.

In Example 3, the gas sensor of Examples 1 or 2 may further include a first pair of contact pads formed over the substrate and electrically coupled to the optical source and a second pair of contact pads formed over the substrate and electrically coupled to the optical detector.

In Example 4, the gas sensor of Examples 1-3, where the optical source may include a first semiconductor diode and the optical detector may include a second semiconductor diode.

In Example 5, the gas sensor of Examples 1-4, where the plurality of optical cavities may be implemented as a photonic crystalline structure.

In Example 6, the gas sensor of Examples 1-5, where the plurality of optical cavities may include a perforation in the substrate with a series of plate-like structures partitioning the perforation.

In Example 7, a temperature sensor, which may include a substrate, an optical source, an optical detector, a plurality of optical cavities in the substrate where the plurality of optical cavities may be arranged in an optical path between the optical source and the optical detector, and a processing circuit which may be coupled to the optical detector and configured to process an optical signal received by the optical detector and to determine a temperature based on the received signal.

In Example 8, the temperature sensor of Example 7 may further include a first pair of contact pads formed over the substrate and electrically coupled to the optical source and a second pair of contact pads formed over the substrate and electrically coupled to the optical detector.

In Example 9, the temperature sensor of Examples 7 or 8, where the plurality of optical cavities may include a perforation in the substrate with a series of plate-like structures partitioning the perforation.

In Example 10, the temperature sensor of Examples 7-9, where the optical source may be configured to generate an optical source signal transmitted to the optical detector.

In Example 11, the temperature sensor of Examples 7-10, may further include a photonic crystalline structure which may include the plurality of optical cavities, where each optical cavity from the plurality is filled by a gaseous substance.

In Example 12, the temperature sensor of Examples 7-11, where the processing circuit may be configured to detect a change in ambient temperature outside the photonic crystalline structure based on a change in the refractive index of the gaseous substance.

In Example 13, the temperature sensor of Examples 7-12, where the ambient pressure inside each optical cavity from the plurality may be greater than the ambient pressure outside each optical cavity from the plurality.

In Example 14, the temperature sensor of Examples 7-13, where each optical cavity from the plurality may be capable of sustaining a pressure above 100 kPa.

In Example 15, a pressure sensor, which may include a substrate, an optical source, an optical detector, a plurality of optical cavities in the substrate where the plurality of optical cavities is arranged in an optical path between the optical source and the optical detector, and a processing circuit coupled to the optical detector and configured to process an optical signal received by the optical detector and to determine a pressure based on the received signal.

In Example 16, the pressure sensor of Example 15 may further include a first pair of contact pads formed over the substrate and electrically coupled to the optical source and a second pair of contact pads formed over the substrate and electrically coupled to the optical detector.

In Example 17, the pressure sensor of Examples 15 or 16 may further include a photonic crystalline structure which may include the plurality of optical cavities, where each optical cavity from the plurality may be filled by a gaseous substance.

In Example 18. the pressure sensor of Examples 15-17, where the photonic crystalline structure may be configured to deflect in at least one surface of the photonic crystalline structure due to a change in ambient pressure outside the plurality of optical cavities.

In Example 19, a method of forming a gas sensor may include forming a substrate, providing an optical source, providing an optical detector, forming a plurality of optical cavities in the substrate or in a layer structure over the substrate, arranging the plurality of optical cavities in an optical path between the optical source and the optical detector and coupling a gas detector to the optical detector and configuring said gas detector to receive a signal representing an optical signal received by the optical detector and to determine if one or more predefined gases are present in the plurality of optical cavities based on the received signal.

In Example 20, the method of Example 19, where the optical source may be configured to generate an optical source signal transmitted to the optical detector.

In Example 21, the method of Examples 19 or 20, may further include forming a first pair of contact pads over the substrate and electrically coupling the first pair of contact pads to the optical source and a forming a second pair of contact pads over the substrate and electrically coupling the second pair of contact pads to the optical detector.

In Example 22, the method of Examples 19-21 where the optical source may include a first semiconductor diode the optical detector may include a second semiconductor diode.

In Example 23, the method of Examples 19-22, where the plurality of optical cavities may include a photonic crystalline structure.

In Example 24, the method of Examples 19-23, where the plurality of optical cavities may include a perforation in the substrate with a series of plate-like structures partitioning the perforation.

In Example 25, a method of forming a temperature sensor, the method may include forming a substrate, providing an optical source, providing an optical detector, forming a plurality of optical cavities in the substrate, arranging the plurality of optical cavities is in an optical path between the optical source and the optical detector, and coupling a processing circuit to the optical detector and configuring the processing circuit to process an optical signal received by the optical detector and to determine a temperature based on the received signal.

In Example 26, the method of Example 25 may further include forming a first pair of contact pads over the substrate and electrically coupling the first pair of contact pads to the optical source and forming a second pair of contact pads over the substrate and electrically coupling the second pair of contact pads to the optical detector.

In Example 27, the method of Examples 25 or 26, where the plurality of optical cavities may include a perforation in the substrate with a series of plate-like structures partitioning the perforation.

In Example 28, the method of Examples 25-27, where the optical source may be configured to generate an optical source signal transmitted to the optical detector.

In Example 29, the method of Examples 25-28 may further include forming a photonic crystalline structure which may include the plurality of optical cavities and filling each optical cavity from the plurality with a gaseous substance.

In Example 30, the method of Examples 25-29, where the processing circuit may be configured to detect a change in ambient temperature outside the photonic crystalline structure based on a change in the refractive index of the gaseous substance.

In Example 31, the method of Examples 25-30, wherein the ambient pressure inside each optical cavity from the plurality may be greater than the ambient pressure outside each optical cavity from the plurality.

In Example 32, the method of Examples 25-31, where each optical cavity from the plurality may be capable of sustaining a pressure above 100 kPa.

In Example 33, a method of forming a pressure sensor may include forming a substrate; providing an optical source; providing an optical detector; forming a plurality of optical cavities in the substrate; arranging the plurality of optical cavities is in an optical path between the optical source and the optical detector; and coupling a processing circuit to the optical detector and configuring the processing circuit to process an optical signal received by the optical detector and to determine a pressure based on the received signal.

In Example 34, the method of Example 33 may further include forming a first pair of contact pads over the substrate and electrically coupling the first pair of contact pads to the optical source and forming a second pair of contact pads over the substrate and electrically coupling the second pair of contact pads to the optical detector.

In Example 35, the method of Examples 33 or 34, where the plurality of optical cavities may include a perforation in the substrate with a series of plate-like structures partitioning the perforation.

In Example 36, the method of Examples 33-35, where the optical source may be configured to generate an optical source signal transmitted to the optical detector.

In Example 37, the method of Examples 33-36 may further include forming a photonic crystalline structure comprising the plurality of optical cavities and filling each optical cavity from the plurality with a gaseous substance.

In Example 38, the method of Examples 33-37, where the processing circuit may be configured to detect a change in ambient temperature outside the photonic crystalline structure based on a change in the refractive index of the gaseous substance.

In Example 39, the method of Examples 33-38, where the ambient pressure inside each optical cavity from the plurality may be greater than the ambient pressure outside each optical cavity from the plurality.

In Example 40, the method of Examples 33-39, where each optical cavity from the plurality may be capable of sustaining a pressure above 100 kPa.

In Example 41, a method of forming a sensor, the method may include forming a substrate, providing an optical source, providing an optical detector, forming a plurality of optical cavities in the substrate or in a layer structure over the substrate, arranging the plurality of optical cavities in an optical path between the optical source and the optical detector, and coupling a processing device to the optical detector and configuring said processing device to receive a signal representing an optical signal received by the optical detector.

In Example 42, the method of Example 41 may further include forming a first pair of contact pads over the substrate and electrically coupling the first pair of contact pads to the optical source and forming a second pair of contact pads over the substrate and electrically coupling the second pair of contact pads to the optical detector.

In Example 43, the method of Examples 41 or 42, where the plurality of optical cavities may include a perforation in the substrate with a series of plate-like structures partitioning the perforation.

In Example 44, the method of Examples 41-43 may further include forming a photonic crystalline structure which may include the plurality of optical cavities and filling each optical cavity from the plurality with a gaseous substance.

In Example 45, the method of Examples 41-44, where the processing device may be configuring to process an optical signal received by the optical detector and to determine a pressure based on the received signal.

In Example 46, the method of Examples 41-45, where the processing device may include a gas detector configured to receive a signal representing an optical signal received by the optical detector and to determine if one or more predefined gases are present in the plurality of optical cavities based on the received signal.

In Example 47, the method of Examples 41-46, where the processing device may be configuring to process an optical signal received by the optical detector and to determine a temperature based on the received signal.

What is claimed is:

1. A gas sensor, comprising:
a substrate;
an optical source;
an optical detector;
at least one photonic crystalline structure in the substrate or in a layer structure over the substrate, the at least one photonic crystalline structure comprising
a plurality of optical cavities in the substrate or in a layer structure over the substrate, each cavity substrate having a hollow interior portion, wherein the hollow interior portions are not in gas communication with each other;
wherein the plurality of optical cavities is arranged in an optical path between the optical source and the optical detector; and
a gas detector coupled to the optical detector and configured to receive a signal representing an optical signal received by the optical detector and to determine if one or more predefined gases are present in the plurality of optical cavities based on the received signal.

2. The gas sensor of claim 1,
wherein the optical source is configured to generate an optical source signal transmitted to the optical detector.

3. The gas sensor of claim 1, further comprising:
a first pair of contact pads formed over the substrate and electrically coupled to the optical source and a second pair of contact pads formed over the substrate and electrically coupled to the optical detector.

4. The gas sensor of claim 1,
wherein the optical source comprises a first semiconductor diode; and
wherein the optical detector comprises a second semiconductor diode.

5. The gas sensor of claim 1,
wherein the plurality of optical cavities comprises a perforation in the substrate with a series of plate-like structures partitioning the perforation.

6. A method of forming a sensor, the method comprising:
forming a substrate;
providing an optical source;
providing an optical detector;
forming at least one photonic crystalline structure in the substrate or in a layer structure over the substrate, the at least one photonic crystalline structure comprising a plurality of optical cavities in the substrate or in a layer structure over the substrate, each cavity substrate having a hollow interior portion, wherein the hollow interior portions are not in gas communication with each other;
arranging the plurality of optical cavities in an optical path between the optical source and the optical detector; and
coupling a processing device to the optical detector and configuring said processing device to receive a signal representing an optical signal received by the optical detector.

7. The method of claim 6, further comprising:
forming a first pair of contact pads over the substrate and electrically coupling the first pair of contact pads to the optical source and forming a second pair of contact pads over the substrate and electrically coupling the second pair of contact pads to the optical detector.

8. The method of claim 6, further comprising:
forming one photonic crystalline structure comprising the plurality of optical cavities.

9. The gas sensor of claim 1, comprising a plurality of photonic crystalline structures, each of the plurality of photonic crystalline structures comprising one of the plurality of optical cavities.

10. The gas sensor of claim 9, wherein the plurality of photonic crystalline structures comprises photonic crystals of varying dimensions.

11. The gas sensor of claim 1, comprising one photonic crystalline structure comprising the plurality of optical cavities.

12. The gas sensor of claim 1, wherein the at least one photonic crystalline structure comprises a one-dimensional photonic crystalline structure.

13. The gas sensor of claim 1, wherein the at least one photonic crystalline structure comprises a two-dimensional photonic crystalline structure.

14. The gas sensor of claim 1, wherein the at least one photonic crystalline structure comprises a three-dimensional photonic crystalline structure.

15. The gas sensor of claim 1, wherein the hollow interior portion of each of the plurality of optical cavities is filled with a gaseous substance.

16. The gas sensor of claim 1, wherein the hollow interior portion of each of the plurality of optical cavities is filled with a fluid.

17. The gas sensor of claim 1, wherein the hollow interior portion of each of the plurality of optical cavities is gas tight.

18. The method of claim 6, further comprising:
forming a plurality of photonic crystalline structures, each of the plurality of photonic crystalline structures comprising one of the plurality of optical cavities.

19. The method of claim 17, wherein the plurality of photonic crystalline structures comprises photonic crystals of varying dimensions.

20. The method of claim 6, further comprising:
forming one photonic crystalline structure comprising the plurality of optical cavities.

21. The method of claim 6, wherein the hollow interior portion of each of the plurality of optical cavities is filled with a gaseous substance.

22. The method of claim 6, wherein the hollow interior portion of each of the plurality of optical cavities is filled with a fluid.

23. The method of claim 6, further comprising:
forming the hollow interior portion of each of the plurality of optical cavities by laser drilling.

24. The method of claim 6, wherein the hollow interior portion of each of the plurality of optical cavities is gas tight.

* * * * *